United States Patent [19]

Kurtz

[11] Patent Number: 5,224,922
[45] Date of Patent: Jul. 6, 1993

[54] QUASISTATIC BIOLOGICAL CELL AND TISSUE MODIFIER

[76] Inventor: Warren H. Kurtz, 761 Ridge Rd., Lyndhurst, N.J. 07071

[21] Appl. No.: 195,831

[22] Filed: May 19, 1988

[51] Int. Cl.$^5$ .............................................. A61N 2/04
[52] U.S. Cl. ........................................ 600/13; 600/14; 128/898
[58] Field of Search ................. 600/9, 13, 14, 15; 128/419 F, 421, 847, 898

[56] References Cited

U.S. PATENT DOCUMENTS

| 4,105,017 | 8/1978 | Ryaby et al. | |
|---|---|---|---|
| 4,266,532 | 5/1981 | Ryaby et al. | |
| 4,428,366 | 1/1984 | Findl et al. | |
| 4,501,265 | 2/1985 | Pescatore | 600/14 |
| 4,641,633 | 2/1987 | Delgado | |
| 4,932,951 | 6/1990 | Liboff et al. | 600/13 |

FOREIGN PATENT DOCUMENTS

| 2707574 | 8/1978 | Fed. Rep. of Germany | 600/14 |
|---|---|---|---|
| 2736345 | 2/1979 | Fed. Rep. of Germany | 600/13 |
| 3231837 | 4/1984 | Fed. Rep. of Germany | 600/13 |
| 80/01648 | 8/1980 | World Int. Prop. O. | 600/13 |

Primary Examiner—David M. Shay
Attorney, Agent, or Firm—Banner, Birch, McKie & Beckett

[57] ABSTRACT

A quasistatic biological cell and tissue modifier is provided that presents a controlled electromagnetic environment which produces beneficial effects in biological material. The electromagnetic environment consists of a static magnetic field and a time-varying field. The static magnetic field potentiates the effect of the time-varying magnetic field and further modulates the amplitude at which the time-varying field is biologically active. The static field is provided by a permanent magnet or through electromagnetic means. In one embodiment the coil that produces the time-varying field is a single coplanar helical coil. In another embodiment it is a plurality of coplanar helical coil segments connected in parallel. In these two embodiments the coil is a flexible printed circuit that can be contoured around an organ. The static magnetic component is provided by a flexible permanent magnet or by the net bias of the time-varying field itself. A third embodiment with two small rigid coils uses a clamp to attach the coils to a patient's ear or other part of the body.

16 Claims, 8 Drawing Sheets

QUASISTATIC BIOLOGICAL CELL AND TISSUE MODIFIER

BACKGROUND OF THE INVENTION

The present invention relates generally to the field of bioelectromagnetics and more specifically to those systems designed to expose biological systems to biologically active electromagnetic fields in order to achieve beneficial clinical effects.

Time-varying magnetic fields are known to modify the behavior of cells and tissues. Biological activity due to a magnetic field is a function of both field amplitude and frequency.

When the amplitude of magnetic field changes, an electric field is induced in a conductive body such as a biological system. This electric field is an energy input into the system. Heretofore, it has widely been held that the resultant biological activity resides solely in the specifications of the resultant electric field. Toward devising systems that exploit the positive effects of induced electric fields in biological systems a number of solutions have been offered. Among these are R. Ryaby, et al. (U.S. Pat. No. 4,105,017), E. Findl (U.S. Pat. No. 4,428,366) and J. Delgado (U.S. Pat. No. 4,641,633). However, each of these patents stresses the primary of the induced electric field and disregards the biological activity of the magnetic field itself. It will be demonstrated in what follows that the electrical component need not be rigorously specified and that both the magnetic component of a time-varying field and an independent static magnetic field can and do contribute to the biological activity of a time-varying magnetic field in such a way that allows for the invention of a new and useful quasistatic biological cell and tissue modifier. Generally one embodiment of the invention is directed to a static magnetic field which modulates the effects of a time varying magnetic field to provide the ability to input more biologically meaningful energy into a system. Alternatively, it will be shown that a single time varying magnetic field may be used to accomplish similar results.

The inventor has observed that placing in-vitro nerve cultures or animals within Helmholtz coils and passing current through the coils to produce a magnetic pulse with a duration of 20 milliseconds, a flux density of between 0.4–3.0 gauss and a repetition rate of 2 Hertz has produced a number of enhanced regeneration responses. For instance, neuritic outgrowth of chick dorsal root ganglia cells in-vitro is enhanced by 35%; scar formation in transected and/or repaired sciatic nerves in rats and cats is reduced; the proportions of important biological molecules in regenerating sciatic nerves of rats is markedly shifted; the rate of axonal sprouting in a rat model where the sciatic nerve is crushed increased by 22%; and the ability of rats to recover from a transected sciatic nerve injury is enhanced by 15–20% as measured by performance in gait after short term postoperative treatment. The amount of scarring in a wound site of a rat is reduced; and the survival of tissue in a rat skin flap model is promoted by 33% due to increased blood circulation.

Preferably the flux density of the pulse is maintained at a constant intensity for approximately 20 milliseconds. The essential nature of the magnetic field dosage per se, can be demonstrated by shortening the pulse to 5 milliseconds. Whereas a pulse of 20 milliseconds at 0.4 gauss repeating at 2 Hertz enhances the growth of chick dorsal root ganglia in culture, a pulse of 5 milliseconds, but other identical, has no biological activity in this system whatsoever. Note that the duration of the pulse only affects the ambient magnetic field, not the induced voltage since this voltage is determined only by the rate of change of the pulse rise and fall.

In addition, if the rate of change of the pulse rise and fall were each reduced by two-fold or more while maintaining the pulse width at 20 milliseconds, there would be no change in the biological activity of the signal: 35% growth enhancement effect would be observed. This is an indication of the nonspecific nature of the induced electric field.

Furthermore, imposing a static magnetic field of 0.6 gauss in the same direction as the pulse field produces an even greater regeneration response in the in-vitro nerve culture system. Under these conditions growth enhancement of 60% was observed. However, the static magnetic field by itself did not produce an effect. This observation demonstrates that the time-varying field is necessary, albeit in a nonspecific manner, and that the static magnetic component of a quasistatic electromagnetic cell and tissue modifier can potentiate the biological activity characteristic of the time-varying component.

Subsequent to these findings, Polk raised the possibility that the biological activity of low frequency time-varying magnetic fields may stem from an interaction with the static component of the earth's geomagnetic field, which is on the order of 0.3–0.5 gauss. Polk pointed out that important biological ions such as calcium could be placed into cyclotron resonance with the time-varying field according to the equation $$f = \frac{B\,q/m}{2\pi},$$

where B is the field strength of the static magnetic component parallel to the time-varying field vector, q/m is the charge to the mass ratio for a particular ionic species, and f is the cyclotron resonance frequency. (Polk C., Bioelectromagnetics Soc., 6th Annual Meeting, p. 77, 1984; URSI XXI General Assembly Abstract, p. 25, 1984). A necessary condition for cyclotron resonance requires that a time-varying electric field be perpendicular to a static magnetic field. The condition is met by a static magnetic field and time-varying magnetic field with parallel components, since a time-varying field induces an electric field perpendicular to its own magnetic vector.

Blackman later reported that static magnetic fields on the order of the earth's geomagnetic field strength did indeed alter the frequency at which a time-varying field possessed biological activity. However, this was not due to a cyclotron resonance effect since the static field and time-varying field were at right angles to one another (Blackman, C. F., et al., Bioelectromagnetics, 6: 327–337, 1985).

Liboff pursued the idea of cyclotron resonance and has since published several papers expanding upon the theory and demonstrating its practical application. (Liboff, A. R., in Interactions Between Electromagnetic Fields and Cells, Chiabrera, A., et al eds, Plenum Press 1985; McLeod, B. R., and Liboff, A. R., Bioelectromagnetics 7: 177–189, 1986; Smith, S. D., et al, Bioelectromagnetics 8: 215–227, 1987).

Other models have theorized that the interaction between a low intensity time-varying magnetic field and static magnetic field can affect the motion of an ion near its membrane binding site through the magnetic component of the Lorentz force (Chiabrera, A., et al., in Interactions Between Electromagnetic Fields and Cells, Chiabrera, A., et al, eds, Plenum Press (1985). As a further development, Polk has attempted to explain the results of Blackman by postulating an ion precessional magnetic resonance mechanism, where resonant frequencies occur at one-half the cyclotron resonant frequency. (Polk, C. Abst., Trans. Bioelectric Repair and Growth Society, Pg. 23, 1987).

It is reasonable to assume that both cyclotron resonance and ion precessional magnetic resonance constitute conditions sufficient to produce biological activity, although it is quite clear that neither is strictly necessary. There are many reports of signals not near either resonance condition that possess biological activity. However, the resonance systems hint at a deep underlying mechanism associated with what is referred to as the "frequency window", since both modes exhibit biological activity at odd harmonics only. The reason for this is not understood at this time. So while progress has been made toward understanding the nature of the frequency window, the problem is far from resolved.

Much less understood and about which little attention has been focused, is the nature of the "amplitude window", which refers to the intensity of a biologically active electric or magnetic field. The amplitude of a time-varying magnetic field at which biological activity is conveyed appears to be windowed within low amplitude ranges near geomagnetic field strengths. Findings of this nature are useful in speculating about natural mechanisms that may have evolved between living systems and the earth's geomagnetic environment. For instance, Smith et al, (see reference above) using a cyclotron resonance system found a peak in the biological activity of the time-varying field at approximately 0.2 gauss.

Toward controlling the earth's geomagnetic field, these authors first cancelled the ambient field and then added precisely defined magnetic field strengths to the environment. Three pairs of coils in Helmholtz flux-aiding configuration were used. Two pairs of bucking coils were used to nullify the horizontal (x-axis) and vertical (y-axis) components of the earth's magnetic field density. The y-axis (east-west) was brought to zero by orienting the x-axis directly along the north-south axis of the earth's magnetic field. Thus, precise regulation of field strengths and orientations are necessary to produce resonance conditions in the geomagnetic range, since the earth's field is comparable in strength to the imposed conditions.

In fact, practically all of the experiments reported display an intense focus on low-level fields at or not far from geomagnetic conditions. This has limited the scope of clinical bioelectromagnetics because low-level fields deposit only miniscule amounts of biologically active energy into living systems and presents practical problems as discussed above. At present no methods have been reported to modulate the amplitude at which a time-varying magnetic field is biologically active. However, according to a novel aspect of the present invention a method for increasing or decreasing the intensity of the time-varying field while maintaining biological activity according to specific cellular mechanisms is given below. The distinct advantages of the method are illustrated with specific examples.

Due to certain inherent characteristics of a system, some systems demonstrate amplitude windows that appear relatively fixed, while other systems have amplitude windows that appear relatively not fixed.

Consider the situation where an important ion such as calcium is either electrogenically driven into the cell through specific channels or where fields trigger mechanisms that allow the ion to enter through voltage sensitive gating processes. The change in internal calcium can cause many effects, but if the concentration exceeds specific levels, the cell will react by actively pumping out calcium in order to maintain ionic homeostasis. Thus, a relatively high amplitude time-varying field that forces calcium into the cell may appear inactive since the cell counteracts the effect of the field. Likewise, an excessive induced voltage would not trigger a voltage sensitive gating mechanism, since an electric field beyond the ranges of the amplitude window would not be recognized as biological information. In these cases it is appropriate to consider the electrical amplitude window fixed. The innovation here is that the amplitude of the time-varying magnetic field can actually be decreased if the static magnetic field strength is increased. Although this phenomenon is not limited to resonant conditions, it is easier to explain and easier to understand if such an example is given.

According to the equations given above, an increase in the static magnetic field necessitates a proportional increase in the resonant frequency. This means that more electrical energy will be induced in a living system at a given magnetic amplitude since the electric field intensity is proportional to the rate of change of the magnetic field, $E \alpha dB/dt$. So if the amount of calcium, for instance, that enters the cell is related to the field intensity through voltage sensitive gating processes, or through an induced calcium current wherein only limited amounts of calcium entry produce an observable effect, then it can be seen that the amplitude of the time-varying magnetic carrier must be decreased in order to maintain the electric field intensity within the appropriate range.

Similar arguments independent of resonance considerations can be made on the basis of the Lorentz force and the velocity imparted to an ion by the induced electric field. Basically, if the magnitude of the Lorentz force affects a critical cell function such as membrane mediated ion binding, then a higher static interacting with an ion at lower velocity still produces a Lorentz force in the appropriate range. The Lorentz force is given by $F = qv \times B$, where q is the charge of the particular ion, v is its velocity and B is the static magnetic field amplitude. The magnitude of the force is given by the vector cross produce.

Exposing cells and tissues with relatively fixed amplitude windows to static magnetic field strengths, greater than geomagnetic field intensities, on the order of at least 3-5 gauss, for example, (although much greater intensities can be used) has significant implications in the design of clinical bioelectromagnetic devices. That is by supplying a relatively high static field from a permanently magnetized material or the like, the energy requirement of the device is reduced, since the magnetic amplitude of the time-varying field can be reduced. Thus, this is a method that facilitates the portability of clinical bioelectromagnetic devices.

This minimum threshold of 3-5 gauss is chosen to keep the variation in the resonance conditions due to the geomagnetic field to less than 10%. While it is preferred to have a tolerance of 10%, greater tolerances could be acceptable in certain circumstances.

Now consider the situation, where due to inherent characteristics of a system, the amplitude window is not fixed. In this situation, the amplitude window of cells and tissues increases with increasing static magnetic field strengths. That is increasing amounts of biologically active energy can be deposited into cells and tissues as the ambient static magnetic environment is increased. This is the method of bietic scaling. (The term bietic scaling also applies to situations where the amplitude window is fixed as described above.) Here, as in the former case, it is instructive to consider voltage sensitive gating processes at the direct effect of electric fields on specific ions. Resonance considerations are offered for simplicity as before.

The motion of an ion in resonance within a specific membrane channel must be confined to certain boundaries and gyroradi in order not to disturb the microenvironment of the channel. For instance, if an electric field were great enough to impart a velocity to the ion such that it challenged the boundaries of the channel, then that channel would cease to function. However, a strong static magnetic field will create a Lorentz force that will constrain the radial motion of an ion. Note that the Lorentz force changes the direction of a charged particle with velocity, v, but does not change the magnitude of the velocity. So at higher frequencies where dB/dt increases, the ion is at higher kinetic and potential energy states, but the path of its motion can be kept in check by the static magnetic field. Therefore, the ion can still pass through the channel, but now it does so at a much higher energy level, which would be otherwise unattainable without the increased field strength of the static environment. Resonance is not a critical factor where it is desired to add energy to a charged particle traversing an ion channel while magnetically constraining the gyropath of the ion to the functional boundaries of the channel.

Voltage sensitive gating processes, which regulate the opening and closing of ion channels, may themselves show a sensitivity to the ambient state magnetic environment. For instance, the endogenous currents of cells generate Hall voltages in the presence of magnetic fields. It is conceivable that these voltages regulate what is observed as a voltage sensitive gate. In this model, the cell possesses properties of a magnetometer. As the ambient magnetic field increases, the Hall voltage increases, thereby raising the voltage amplitude at which the gate becomes sensitive. As the static magnetic field increases in strength, the cell becomes concomittantly responsive to increases in the amplitude of the time-varying magnetic field. Thus, the amount of biologically active energy that can be imparted to cells and tissues as biological information, increases as the static magnetic field increases.

Increasing the intensity of biologically active fields has considerable advantages over state-of-the-art devices. As stated earlier, cells make a strong attempt at maintaining ionic homeostasis. There is no evidence that low intensity devices can overcome cellular homeostasis. That is, at low energy levels, biologically active fields merely act to trigger biological processes that are poised for activation. As such, low intensity devices cannot redirect physiologic processes. On the other hand, high-intensity devices can overcome homeostatic drive and redirect the function of cells and tissues.

Consider for example the transmission of a sensory stimulus across a synaptic junction. The transmission of an action potential is governed by the release of specific neurotransmitters. This release is in turn dependent upon controlled calcium uptake by the axonal membrane at the synapse.

Since calcium concentrations external to the cell are orders of magnitude greater than internal concentrations, membrane channels are either closed or largely concerned with pumping calcium out of the cell in order to maintain homeostasis. Weak biologically active systems can cause a transient and modest increase in internal calcium concentrations, but they are not intense enough either to keep the channels open for prolonged periods or to continually force calcium inward against homeostatic mechanisms. A high intensity biologically active system, on the other hand, can cause enough calcium to enter the cell such that the normal intake associated with neurotransmitter release is prevented by an unfavorable electrogenic gradient. This then leads to the disruption of a sensory signal and a loss of sensation in the area. Thus, an application of bietic scaling, the increasing of the biologically active amplitude window, is toward pain relief. High-intensity biologically active devices offer a means of true electroanesthesia.

Another application of bietic scaling is in the area of bioenergetics, the generation of high energy compounds by cells, Mitochondria produce the bulk of the high energy compound ATP, but only in the presence of oxygen. In the process of oxidative phosphorylation, ADP is converted to ATP by coupling to, or incorporating the energy that is released by a proton traversing the electric gradient of the mitochrondrial membrane. The amount of ATP made is directly related to the energy states of the proton. Adding a significant amount of energy to the proton, either potential or kinetic, increases the amount of ATP synthesized. Thus, the efficiency of cellular energy production is markedly enhanced by high-intensity resonant or non-resonant biologically active time-varying magnetic fields. This is an important consideration in biological systems that are compromised by inadequate oxygen levels.

In effect, through bietic scaling, electromagnetic fields are metabolized to ATP in a manner analogous to photosynthesis, a process termed bietic synthesis. This has many clinical applications in situations that would benefit from increased ATP synthesis, among which are: wound healing, nerve regeneration, compensation of vascular insufficiency, and traumatic ischemia. In the use of bietic scaling, the amplitude of the time-varying magnetic field can be adjusted automatically by the electronic means according to the amplitude of the static magnetic field and visa-versa. In the case where bietic scaling is applied to a fixed amplitude window, the amplitude of the time-varying field can be inversely proportional to the static magnetic field amplitude. For an amplitude window that is not fixed, the amplitude of the time-varying field increases proportionally to the static magnetic field amplitude. If the devices described are being used to generate resonant conditions, the frequency of the time-varying field is also adjusted automatically to the static field strength by means which can be accomplished by those with ordinary skill in the art, for instance, through calibration of the current driving the static magnetic field. Proportionally constants of amplitude to frequency can be preselected to met the conditions required for the chosen resonant ion. For autoresonance signals, the frequency of the signal is calibrated to the net direct current bias of the current that drives the time-varying field.

It is also been reported that applying electric fields to the ear produces neurotransmitter effects that relieve anxiety and addictive behaviors such as drug use and smoking. However, there are definite advantages of using magnetic fields to produce localized electric fields as the foregoing has shown.

SUMMARY OF THE INVENTION

It is, therefore, an overall object of the present invention to provide a quasistatic biological cell and tissue modifier than can expose living systems to biologically active magnetic fields.

A further object is to provide a quasistatic biological cell and tissue modifier that can expose the tissue to time-varying magnetic fields such that the rise and fall times may be relatively nonspecific and may be controlled in part by the inductance of the delivery coil.

A further object is to provide a quasistatic biological cell and tissue modifier that can expose tissue to a time-varying magnetic field such that the rising and falling segments may be separated in time by a constant magnetic flux for a period that renders the signal biologically active.

A further object is to provide a quasistatic biological cell and tissue modifier that can provide a large flux density for a small volume. This may be accomplished by using a device comprising multiple coplanar helical coils.

A further object is to provide a quasistatic biological cell and tissue modifier comprising a magnetic field producing coils that may be contoured to the shape of a portion of a human anatomy.

A further object is to provide a quasistatic biological cell and tissue modifier comprising a magnetic field producing coils that may be attached to a portion of the human anatomy to provide a beneficial neurotransmitter effect.

A further object is to provide a quasistatic biological cell and tissue modifier that can provide a static magnetic component as well as a time-varying magnetic component.

A further object is to provide a quasistatic biological cell and tissue modifier that can modulate the amplitude to biologically active time-varying fields by increasing the static magnetic component beyond geomagnetic levels.

A further object is to provide a quasistatic cell and tissue modifier that produces a single time-varying magnetic field by at least one coil means, such that the resonant frequency of the signal is tuned to its own net positive magnetic bias.

Further objects of the invention will be readily apparent to one of ordinary skill in the art in view of the description of the preferred embodiments of the present invention.

To the accomplishment of the above and related objects, this invention may be embodied in the forms illustrated in the accompanying drawing, attention being called to the fact, however, that the drawings are illustrative only and that changes may be made in the specific constructions illustrated and described within the scope of the appended claims.

BRIEF DESCRIPTION OF THE DRAWINGS

The Figures in the drawings are briefly described as follows.

DETAILED DESCRIPTION OF THE PREFERRED EMBODIMENTS

Figure 1:
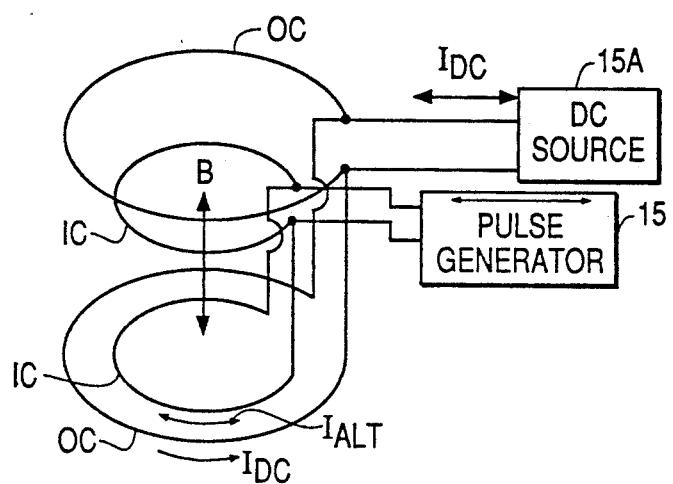
FIG. 1 is a diagrammatic electrical schematic of a portion of the present invention illustrating the generation of a static magnetic field and a time-varying field through electromagnetic coil means.
Figure 1A:
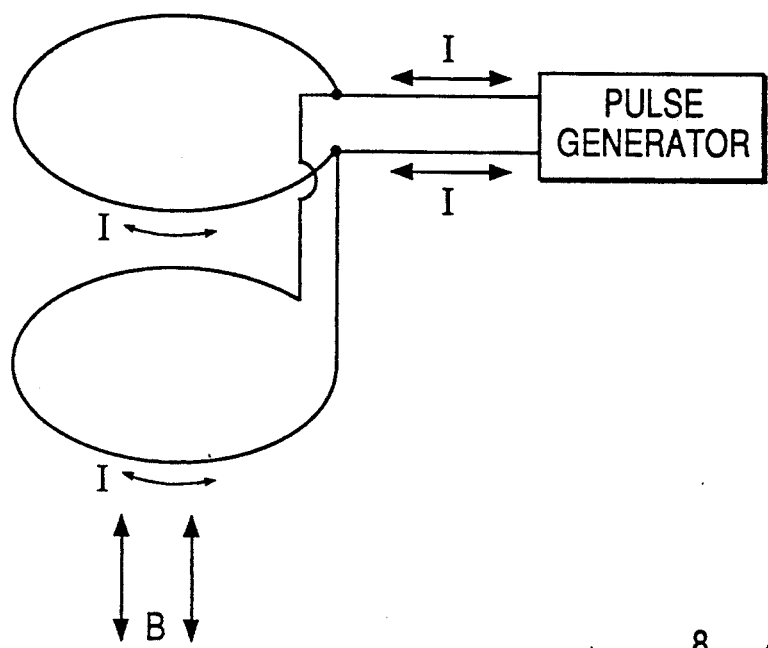
FIG. 1A is an alternate embodiment showing a coil arrangement for producing a single field with a flux aiding configuration.
Figure 7:
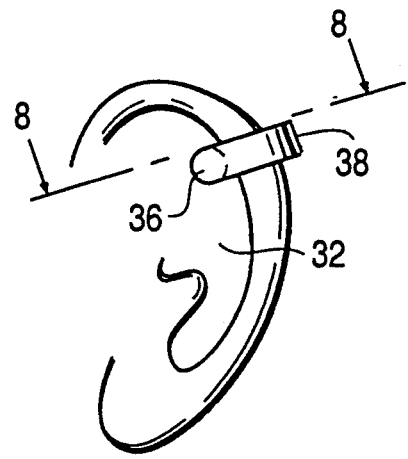
FIG. 7 is a side view of another embodiment of the present invention shown attached to a patient's ear.

In FIG. 1 it is demonstrated that current passing through a conductor arranged as a loop produces a magnetic field perpendicular to the flow of current generated by pulse generator 15 and a DC source 15A (to be described below). This embodiment is shown as paired sets of flux-aiding coils although other configurations will be obvious to one of ordinary skill in the art. Preferably the outer set of coils OC produces a static magnetic field, while the inner set of coils IC produces a time-varying magnetic field indicated collectively as B. Cells, tissues, organs, or regions of a whole organism can be exposed to the afore described beneficial effects of the fields by being placed within the coil apparatus. The sets of coils may be oriented to produce magnetic fields whose vectors are either parallel or perpendicular to one another. Alternatively, a biased time-varying current or a permanent magnet may supply the static magnetic field, thereby eliminating the need for the second coil system. As shown in FIG. 1A, one pair of coils may be used to set up a field comprising a static magnetic component and a time-varying component. This may be done by generating a field driven by a current with a net positive bias. Moreover, in certain situations a non flux aiding configuration can be useful to generate a nonuniform field to expose selected tissue regions to desired amplitudes.

Figure 12:
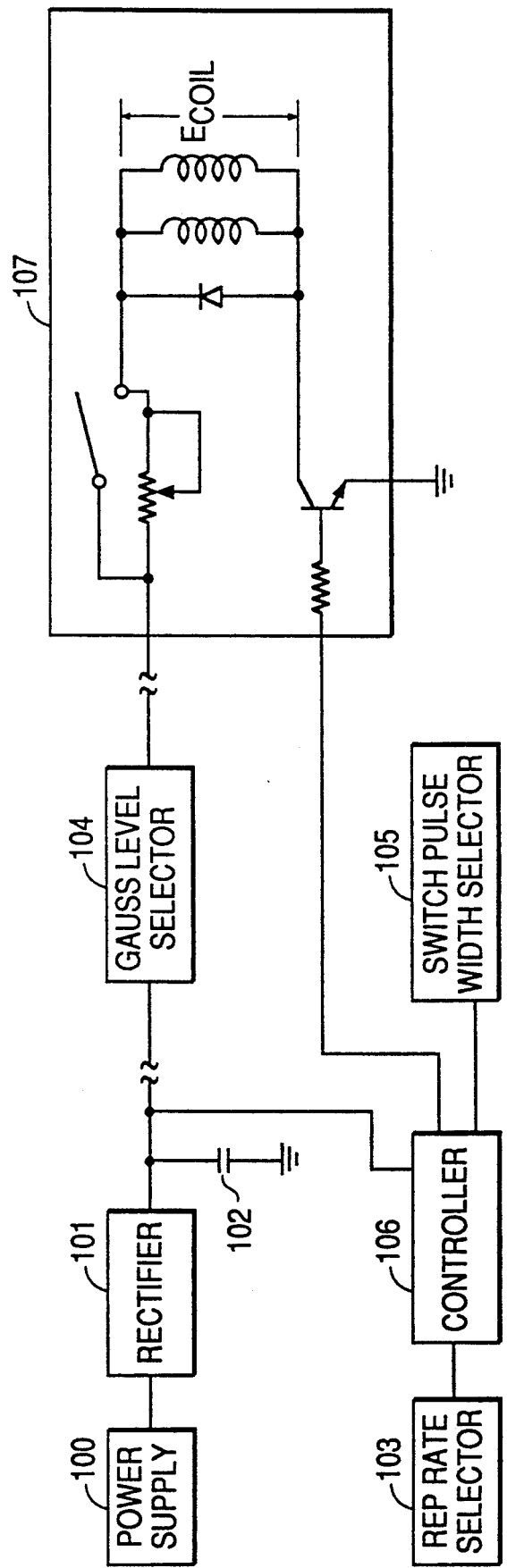
FIGS. 12 and 13 show current generating means for use with various embodiments of the present invention.
Figure 13:
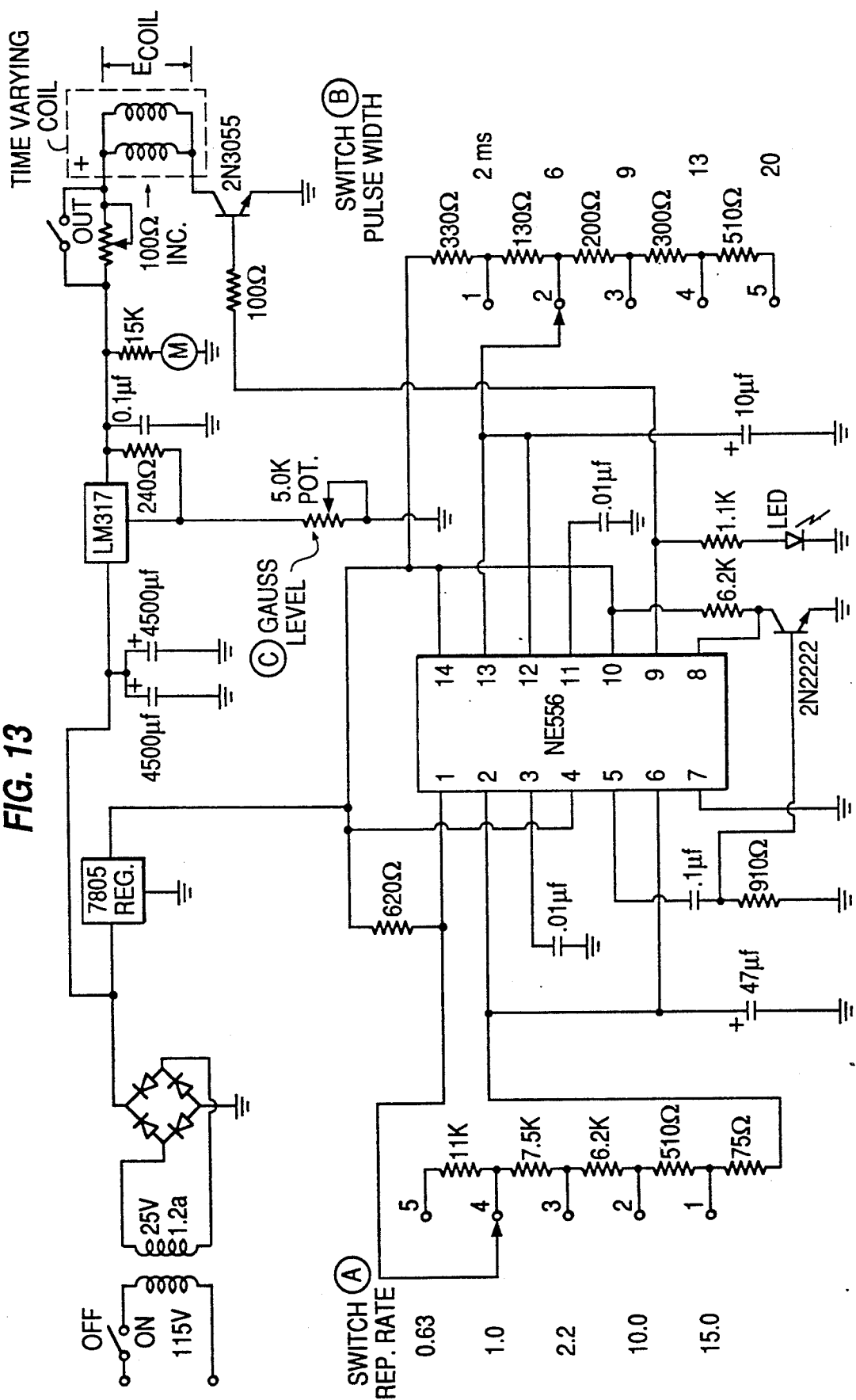

Shown in FIGS. 12 and 13 are block and schematic diagrams for a current pulse generator capable of use with a preferred embodiment of the present invention or other embodiments including but not limited to the single and double coil configurations described above. As seen in FIG. 12 there is a power supply 100, connected to rectifier 101 and capacitor 102. These elements operate in a manner known in the art. Further provided is a repetition rate selector 103, gauss levels selector 104, and switch pulse width selector 105 each of which may be operatively connected to a controller 106. Each of these selectors (103, 104, 105) are variable to select parameters of a pulse signal generated by pulse generator indicated generally as 107. The operation of this circuit will be readily apparent to one of ordinary skill in the art and for the sake of clarity will not be further explained here.

A preferred embodiment for implementing the present invention is shown in FIG. 13. As can be seen, the repetition rate selector and switch pulse width selector are each comprised of a voltage divider network to provide an input into the controller. The gauss level selector may comprise a potentiometer. An output of the controller in conjunction with the gauss level selector, provides pulse shaping information to control the parameters of the output current pulses used to drive the coils that produce the time varying component of the magnetic field in a manner readily apparent to one of ordinary skill in the art.

While this circuit is preferred for generating the pulses in accordance with one embodiment of this invention, it is to be understood that various other types of pulse generators could be used to implement this and other features of the present invention.

A DC supply (not shown) may be used to produce the static magnetic component in a manner that will be apparent to one of ordinary skill in the art. Alternatively an AC biased signal may be used to achieve substantially the same result.

Figure 2:
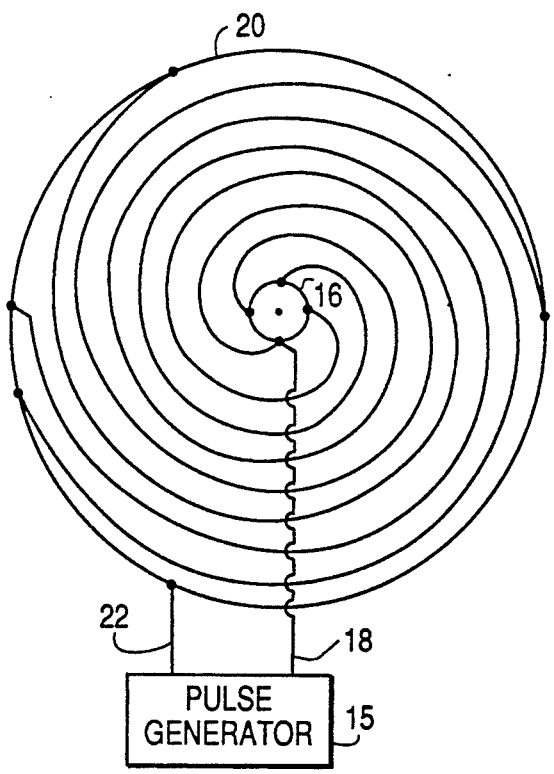
FIG. 2 is a diagrammatic electrical schematic illustrating in further detail a preferred winding configuration of one embodiment of the present invention.
Figure 3:
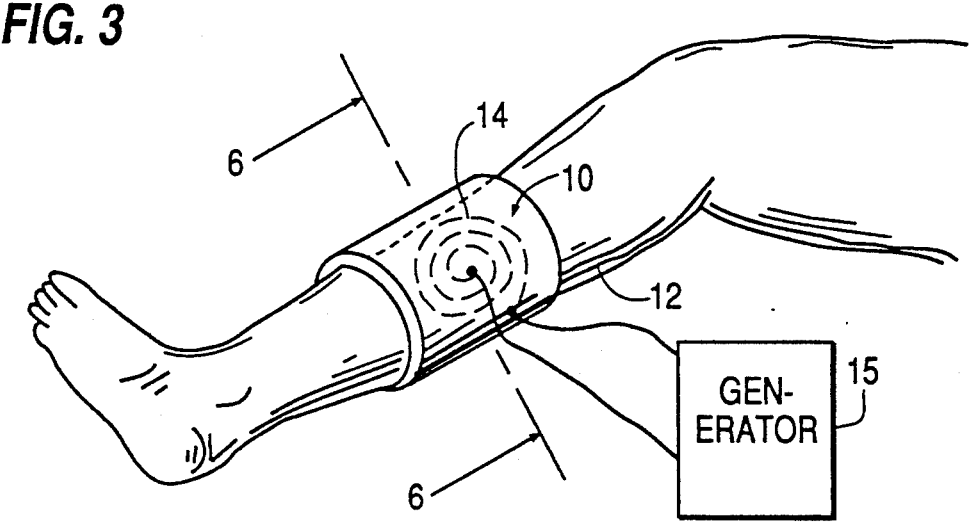
FIG. 3 is a perspective view of one embodiment of the present invention strapped onto a patient's leg.
Figure 4:
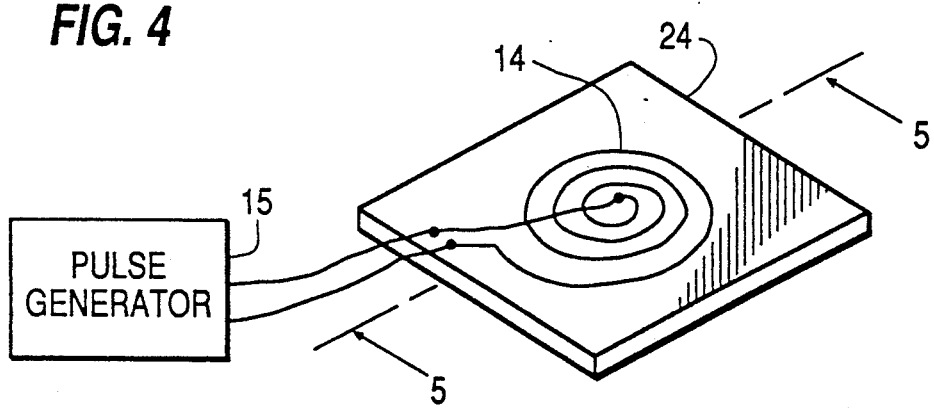
FIG. 4 is a perspective view of a flexible panel portion of the present invention.

FIG. 3 one embodiment of the invention is shown generally indicated as 10 and is wrapped around a patients' calf 12. The device 10 comprises a conductor 14 which may be configured as a single substantially coplanar helix as shown in FIG. 4, or as a plurality of substantially coplanar helical segments as illustrated in FIG. 2. In operation, the device 10 is wrapped around the tissue, organ or organism of a living system (in whole or in part). A pulse generator generates controlled pulses to induce a desired magnetic field so that the portions of the treated subject are exposed to the beneficial effects of the controlled electromagnetic environment to achieve the desired results as described above. The device 10 of FIG. 3 is shown by way of example only. It is to be understood that the size, shape and overall configuration can be varied to accommodate all types of tissue, organs, organisms and living systems that may be subject to the controlled electromagnetic field. It is also to be understood that the generator 15 may be remote from or contained within the device 10.

With reference to FIG. 2, termination of each helical segment may be tied together by a conducting ring 16, connected to wire 18, and the outer termination of each helical segment may be tied together by a conducting ring 20, connected to wire 22. The number of helical segments may be varied as will be obvious to one of ordinary skill in the art. The use of multiple helical segments allows the generation of a large magnetic flux at relatively low voltages since the segments are connected in parallel. A ferromagnetic core (not shown) could be used to enhance the magnetic field, or a fixed permanent magnet could be used to provide an ambient field within the scope of this invention. Either the core or magnet could be located at a position within the device in a manner that will be obvious to one of ordinary skill in the art. Alternatively, additional coils, electrically isolated from the coils illustrated, could be used to generate an ambient field parallel or perpendicular to the other field. FIG. 4 represents the device 10 in its unwrapped state. As seen in FIG. 4, a single substantially coplanar coil is formed on a flexible substrate 24. Respective ends of the coil are connected in a known manner to pulse generating means described else where in this specification.

Figure 5:
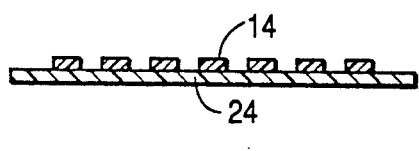
FIG. 5 is a cross sectional view taken on line 5—5 of FIG. 4.
Figure 6:
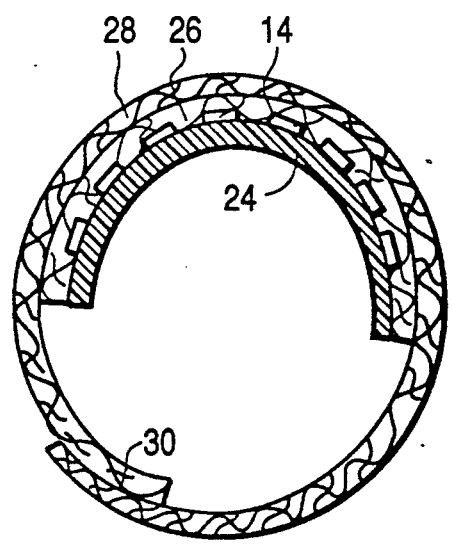
FIG. 6 is an enlarged exaggerated cross sectional view taken on line 6—6 of FIG. 3.

The substrate 24 which may support any embodiment of the coil is made of a flexible material (such as the trademarked KEVLAR) that fits easily around a portion of a living organism. The flexible material itself may further comprise a permanent magnet in a manner known in the art. As illustrated in FIGS. 5 and 6, the coil and substrate can be combined into a flexible substrate 24 using conventional copper clad flexible printed circuit materials and an etch-away process. In a preferred embodiment, flexible printed circuit board (14, 24) is covered by a protective layer 26 (which may be a clear plastic capable of insulating the coils) and a flexible sleeve 28 (which may be comprised of a cloth fabric or other suitable material which) is wrapped around the organ and secured in place at 30 using any convenient fastening means which may be for example hook and loop pile type fastener material or other known means. The embodiment of FIG. 6 can also be adapted to provide for a pair of coils and substrates in an aiding configuration. Alternatively, flexible permanent magnets can be configured to provide a static magnetic field perpendicular to the time-varying field.

Figure 8:
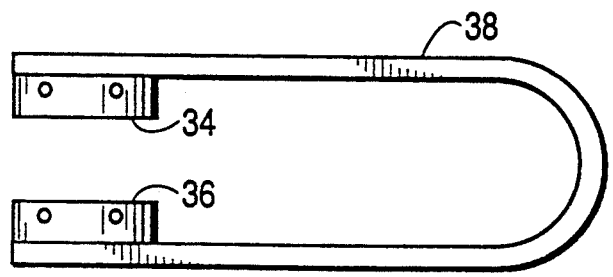
FIG. 8 is a side view of the embodiment of FIG. 7 taken along line 8—8 of FIG. 7; and, FIGS. 9, 10 and 11 are timing diagrams illustrating representative characteristics of the electrical energy used to power the various embodiments of the present invention.

By way of example, in order to expose ear 32, or other similarly shaped parts, to the controlled magnetic field, a pair of rigid coils and magnets such as 34 and 36 in FIG. 8 are used. These coils are held firmly in place by clamp 38 which may be contoured to conform to the shape of the desired part. Clamp 38 may preferably be formed of a flexible plastic material. In this particular embodiment coils 34 and 36 can also be excited at low audio frequencies causing clamp 38 to oscillate and apply mechanical stimulus simultaneously to the wearer's ear. Alternatively, a single rigid magnet and coil, such as 36 could be held in place by any of the conventional mechanisms currently used to hold hearing aids in place such as glasses, behind the ear devices, or intraaural devices that would contain the relevant electronic components. A voltage supply (not shown) as well as on/off and voltage level (current level) control means may be incorporated within the device or may be located remotely therefrom.

Figure 9:
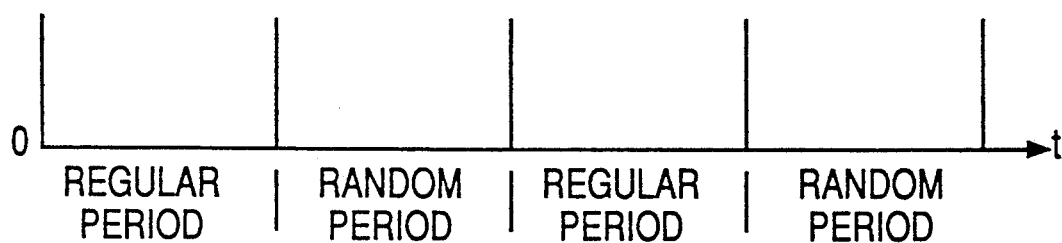

An essential component to the therapeutic success of the invention is the time-varying magnetic field. The current used to excite the coils may be periodic or aperiodic as indicated in FIG. 9, the periodicity referring to the repetition rate of a magnetic pulse. These pulses are produced by pulse generator circuitry within the device or located remotely therefrom. Random periods minimize the opportunity of a living system to adapt and become tolerant to the imposed electromagnetic environment.

Figure 10:
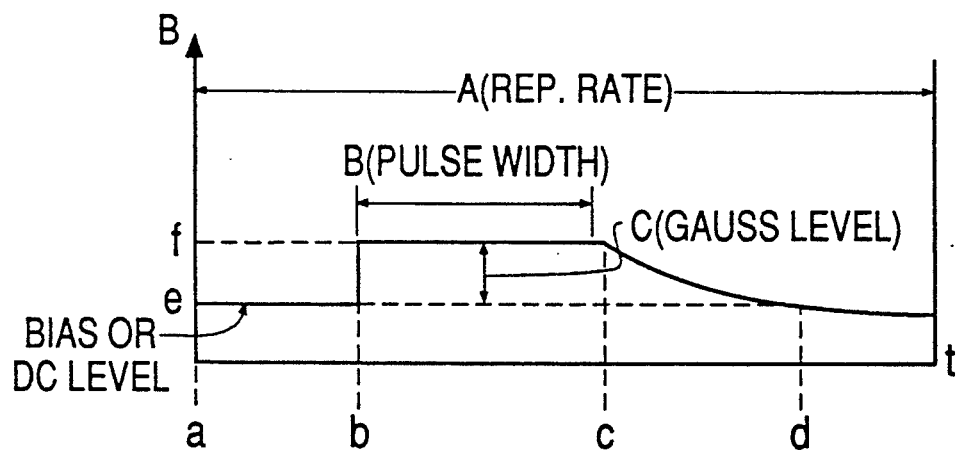

In FIG. 10, from time a to time b there is a steady flow of current so that a static magnetic field of flux density e is generated. This level e represents the level of magnetic flux due to a static component of a magnetic field. It is to be understood that this level can be virtually any value or may be 0 in the absence of a static magnetic field. This e value may be varied by controlling a DC source or by providing a bias to a time varying pulse generation. At time b the circuitry generates a pulse having a specified rise time which causes the magnetic field to take a step from flux density e up to flux density f. The size of this step may be controlled by the Gauss level selector shown in FIG. 12 or 13. At the same time this sudden growth in flux lines induces a positive pulse of voltage into the conductive biological material. The magnetic flux remains at the constant value of f until time c at which time it begins an exponential decay which is preferably slower than the rise time. The delay is a function of the coil inductance and current resistance which may be selected to achieve predetermined characteristics. As the flux lines begin to collapse at time c a smaller negative voltage is induced in the biological material. The negative induced voltage falls to zero by d and the magnetic flux falls to its quiescent value of e.

In addition to the positive effects of the magnetic field itself, the period between b and c provides for a net input of electrical energy for periods of time (e.g. 20 milliseconds) that are biologically meaningful. This time duration may be selected by pulse width selector means in FIGS. 12 or 13. Although all types of inductive systems result in a net electrical input of zero, signals whose positive and negative portions are contiguous in time are suboptimal in depositing useful electrical energy into the cell since the availability of the positive input is rapidly limited by the negative input. In effect, contiguous electrical pulses withdraw the energy almost simultaneously to the deposit. It is therefore preferable to provide a signal that has noncontiugous positive and negative portions. The utilization electrical energy is further optimized by providing for a rise time faster than the fall time, thereby minimizing the amplitude and biological effect of the countervailing electric field of the collapsing magnetic field.

Figure 11:
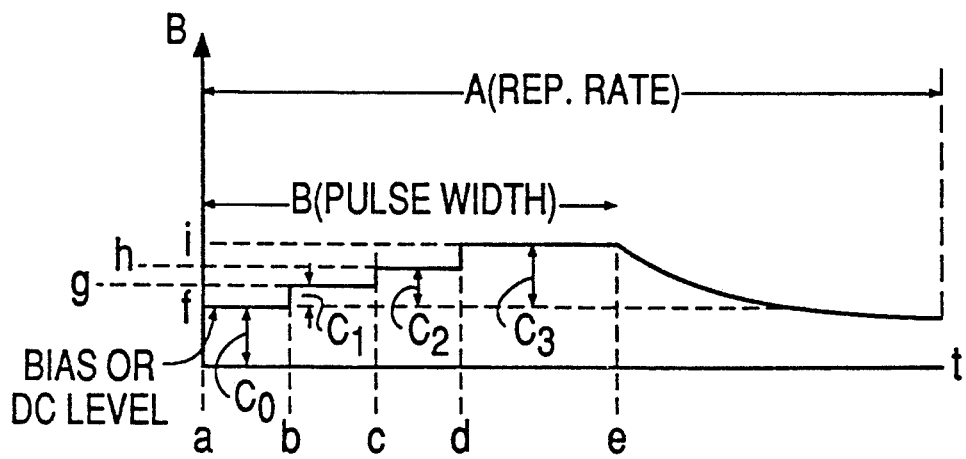

The same reasoning can be applied to the waveform further described in FIG. 11. Current steps each having a specified rise time caused by pulses generated by the current pulse generating circuitry at times b, c, and d generate positive pulses, while the slow decay controlled by chosen inductance and resistance values beginning at time e has little induced effect. Thus, multiple inputs of electrical energy can be utilized before the biological system is discharged by the collapsing field. This stepping of levels enhances and multiplies the effect described with respect to the signal used in FIG. 10. The magnitude of incremental inputs and the time period therebetween may be varied depending on the desired effect and the nature of the biological system by controlling the appropriate selectors (pulse width, gauss level) of FIGS. 12 or 13.

By way of example, in an ambient static magnetic environment, preferred driving voltage values which yield therapeutic results may be: pulse rise time 150 to 400 microseconds, pulse decay time 860 to 920 microseconds, pulse duration 5 to 20 milliseconds, pulse repetition rate 2–16 Hertz. Current rise and fall times are a function of coil inductance and circuit resistance. Typical field values are between 0.4 to 3.0 gauss in low static magnetic environments. Frequencies and amplitudes are regulated in accordance with higher static magnetic field conditions. The ratio of fall (or decay) time to rise time is significant to achieve maximum exposure to useful energy by the cell, tissues or the like. This principle is consistent with the above explanation of noncontiguous waveforms.

The signals exemplified in FIGS. 9, 10 and 11 are illustrative of preferred signals that may be used in conjunction with a preferred embodiment of the present invention. However it is to be understood that many variations may be made to those signals without departing from the scope of the invention. For example, certain signals, even though the positive and negative portions of the electric field are contiguous in time, have distinct advantages.

For instance, an example is a triangular wave with current driven rise and fall times of equal duration. This signal induces a square bidirectional electric wave. The square wave contains harmonics at odd overtones only—precisely the harmonic structure observed in resonant systems. The total energy (Energy Freq$_o$) of a square wave is, therefore, the summation of energy as distributed over all possible biologically active resonant energy bands (harmonic components) and may be expressed as:

$$\text{Energy Freq}_o = A\frac{(Bq)}{2\pi m} + 3B\frac{(Bq)}{2\pi m} = 5C\frac{(Bq)}{2\pi m} + \ldots = \frac{Boq}{2\pi m}$$

Where Bo=static field component, A, B and C are coefficients and m=mass of the particular ion and q=charge. By using a sine wave, on the other hand, the method of bietic scaling can deposit energy into a cell through a single resonant energy band. For the case where the amplitude of the static magnetic field and the amplitude of the time-varying field are equal, the resultant signal is a sine wave biased by the static amplitude. The peak-to-peak amplitude and resonant frequency are related by:

$$\text{Amplitude} = \text{Frequency}\frac{4\pi m}{q}$$

From the example cited, it can be seen that the resonance frequency of the signal can be tuned to its own net magnetic bias. Generalizing to all time-varying magnetic fields with a net positive magnetic bias, it can be seen that in the absence of an independent static field, the cyclotron resonance frequency is directly proportional to the level of net magnetic bias:

Amplitude$_{bias}$ α Frequency

Thus, a biological ion can be placed in resonance by a single time-varying magnetic field interacting with its own static magnetic component. This principle is termed: autoresonance.

With autoresonance, there is no need to superimpose a static magnetic field perpendicular to the time-varying field, since a single field will produce an electric field perpendicular to its own biased magnetic vector. Parallel electric and magnetic vectors are conditions necessary if cyclotron resonance is to occur.

Tuning according to the above can be effected in a manner known in the art. For example, the direct current component of the current waveform driving a biased time-varying magnetic field can be measured directly or calculated. The resultant static field can then be measured directly using the desired coil embodiment, or it can be calculated using the coil specifications by those with ordinary skill in the art.

The use of a single coil rather than a flux-aiding pair creates a situation where the magnetic field is not uniform, falling off in strength with distance from the coil surface plane according to the coil structure and known corresponding mathematical relationships. This allows the resonant conditions to be localized in space by adjusting the amplitude and/or frequency of the signal. Thus, this is a means of focusing the resonant conditions to a selective body site, without affecting extraneous sites.

Figure 14:
FIGS. 14, 14a, 15, 16, 17 and 18 show examples of waveforms useful in understanding features of the present invention.
Figure 14A:
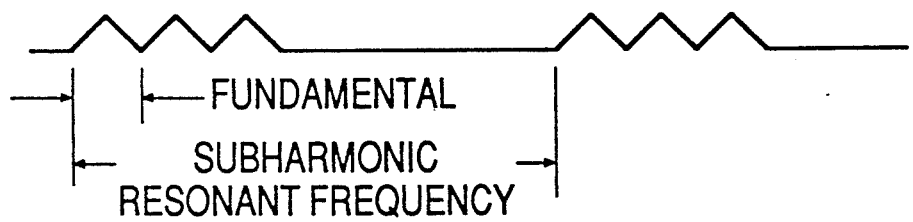

Autoresonance makes it possible to set up resonant conditions with a single field and corresponding apparatus. This has practical advantages in the design and implementation of clinical treatment devices. By increasing the amplitude of the signal beyond geomagnetic levels, the contribution of the earth's magnetic field to the total applied magnetic environment is reduced to the level of tolerable noise. Portability is substantially enhanced, and the need to take the geomagnetic environment into account in terms of field strengths and orientation is obviated by the process of bietic scaling. This eliminates problems encountered with prior portable type devices wherein movement of the subject would realign the device with respect to the earth's geomagnetic field and would necessitate readjusting the resonant conditions with each movement. Subharmonic resonant frequencies may also be used. Either the primary frequency of the waveform can be adjusted to a subharmonic resonant frequency, or the waveform can be grouped as bursts, with the frequency of the bursts being at a subharmonic resonant frequency. Examples are given in FIGS. 14 and 14a. It will be understood that any number of waveforms can be used, and the ones cited are for illustrative purposes.

Figure 15:
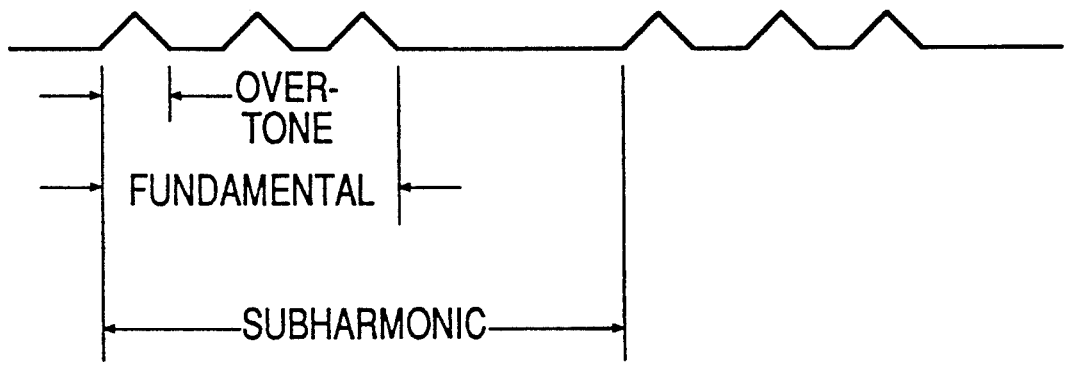

It is understood that combinations of the subharmonics, the fundamental resonant frequency, and overtones can also be used as a single waveform as illustrated in FIG. 15.

Figure 16:
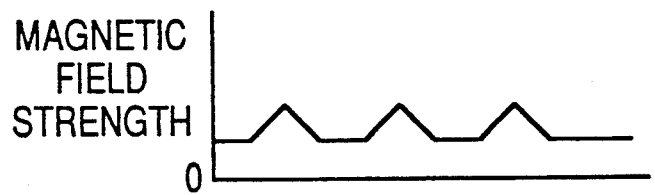
Figure 17:
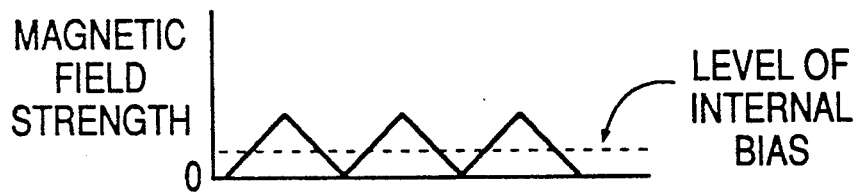

Autoresonant signals are not superimposed onto a static magnetic field as is the waveform illustrated in FIG. 16. Rather, the magnetic bias to which the frequency is tuned is the internal bias of the signal itself, derived from the direct current component of the driving current. This is illustrated in FIG. 17.

Figure 18:
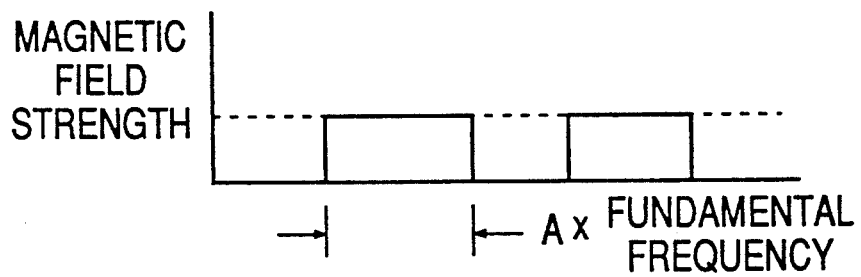

Another example is a squarewave or one that is nearly so. Here the amplitude of the wave can be used to select the resonant frequency. This is shown in FIG. 18. Here, "a" is a coefficient with a value indicating that the wave is of a fundamental frequency, an overtone, or harmonic.

It has been found that there are preferred treatment regimens when a time-varying magnetic field is used to promote the healing of a transected nerve or crushed nerve. Whereas a crushed nerve may be treated immediately after the injury to produce a beneficial response, a transected nerve may require a different treatment schedule to produce beneficial functional responses. For instance, the method and timing of surgical repair of a transected nerve, manipulation of the axonal environment and the timing of electromagnetic treatment are important factors.

An experiment was conducted using a number of surgical techniques and treatment schedules. Eight different groups of animals were used, which are summarized below. All animals were conditioned to the performance of a functional gait analysis prior to their nerve injuries. Animals were then subjected to nerve transection and subsequent repair under microsopic control. The performance on the functional gait analysis was scored at 45, 75, 105, and 140 days post trauma. The results are summarized below.

Experimental Groups

Group I. Immediate repair with vein graft conduit.
Group II. Immediate repair with vein graft conduit plus inhibition of the toxic intracellular entry of calcium with chlorpromazine (CPZ).
Group III. Immediate repair with vein graft conduit plus CPZ plus PEMF 4 hrs./day×5 days.
Group IV. Immediate epineurial repair.
Group V. Immediate epineurial repair plus PEMF 4 hrs./day×5 days.
Group VI. Delayed epineurial repair. (day 5)
Group VII. Delayed epineurial repair plus PEMF 4 hrs./day ×5 days.
Group VIII. Delayed epineurial repair plus PEMF 4 hrs./day × 10 days. (day 0–10).

Results

1. The vein graft conduit was inferior to a standard epineurial repair.
2. Delayed nerve repair was superior to immediate repair in the early study periods, and equivalent at later times.
3. Calcium influx inhibition significantly enhanced early axonal regeneration.
4. The use of PEMF immediately after injury blocked the beneficial effects of calcium influx inhibition.
5. The combination of delayed nerve repair and PEMF improved locomotion both in the early and later study periods.
6. The combined use of calcium influx inhibition, delayed nerve repair, and prolonged PEMF may be a superior treatment for nerve injuries.

It has also been noted that when a nerve has been crushed the relative orientation of the animal in the field was not a factor. Varying the length of treatment from 1–10 hrs. per day after the trauma did not effect the beneficial outcome. Of clinical significance was the finding that pretreatment of the animal before injury without treatment after the injury results in substantially the same benefit. This has application in elective surgical procedures where pretreatment would benefit the recovery period.

While certain novel features of this invention have been shown and described and are pointed out in the annexed claims, it will be understood that various omissions, substitutions and changes in the forms, details and operation of the device illustrated can be made by those skilled in the art without departing from the spirit of the invention.

I claim:

1. A method for producing a regenerative effect in a biological system by exposing said biological system to an electromagnetic environment, said method comprising the steps of:
   generating a time-varying magnetic field;
   generating a static magnetic field in conjunction with said time-varying magnetic field in order to produce said regenerative effect.

2. A method for exposing a biological system to an electromagnetic environment to produce a regenerative effect in said biological system, said method comprising the steps of:
   generating a time-varying magnetic field comprising unidirectional magnetic pulses; and
   generating a static magnetic field in conjunction with said time-varying magnetic field in order to produce said effect in said biological system.

3. The method of claim 2 wherein said unidirectional magnetic pulses are generated at a repetition rate substantially equal to a subharmonic of a selected ion precessional magnetic resonance frequency.

4. The method of claim 2, wherein said unidirectional magnetic pulses are substantially square.

5. The method of claim 2 wherein said step of generating said unidirectional magnetic pulses comprises generating at least a first component having a rising level, a second component having a substantially constant level and a third component having a falling level, said first and third components having rise and fall times respectively.

6. The method of claim 5 wherein said second component is generated with a duration that is substantially a reciprocal of a selected ion precessional magnetic resonance frequency.

7. The method of claim 5 wherein said step of generating unidirectional magnetic pulses further comprises generating a unidirectional magnetic pulse such that the fall time of said third component is of greater duration than the rise time of said first component.

8. The method of claim 7 wherein the step of generating unidirectional magnetic pulses further comprises generating voltage pulses having a pulse repetition rate substantially within the range of 0.5-256 Hz, wherein said rise time is substantially within the range of 150-400 microseconds, said fall time is substantially within the range of 860-920 microseconds, and wherein said second component is further defined by a constant duration, wherein said constant duration is substantially within the range of 2-20 milliseconds and said constant level is substantially within the range of 0.1-3.0 gauss.

9. A method for exposing a biological system to an electromagnetic environment to produce a regenerative effect in said biological system, said method comprising the steps of:
generating a time-varying magnetic field;
generating a static magnetic field oriented parallel to said time-varying magnetic field in order to produce said effect in said biological system.

10. A method for exposing a biological system to an electromagnetic environment to produce a regenerative effect in said biological system, said method comprising the steps of:
generating a time-varying magnetic field;
generating a static magnetic field in conjunction with said time-varying magnetic field in order to produce said effect in said biological system, wherein said amplitude level of said static magnetic field is substantially at least an order of magnitude greater than an ambient geomagnetic amplitude level.

11. The method of claim 10 wherein the amplitude level of said time-varying field is less than or equal to the amplitude level of said static magnetic field.

12. A method for producing a regenerative effect in a biological system by exposing said biological system to an electromagnetic environment, said biological system having an amplitude window defining the range of amplitudes of an applied time-varying magnetic field at which said effect will be produced, said method comprising the steps of:
generating a time-varying magnetic field having a selectable amplitude level;
generating a static magnetic field having a selectable amplitude level and being selectably oriented with respect to said time-varying magnetic field to modify said amplitude window and modulate the amplitudes at which said time-varying magnetic field produces said effect in said biological system.

13. The method of claim 12 wherein said static magnetic field is oriented perpendicular to said time-varying magnetic field.

14. The method of claim 12 wherein the amplitude of said static magnetic field is of such a level so as to increase the amplitudes at which said time-varying magnetic field produces said effect in said biological system.

15. The method of claim 12 wherein the amplitude of said static magnetic field is of such a level so as to decrease the amplitudes at which said time-varying magnetic field produces said effect in said biological system.

16. The method of claim 12 wherein said time-varying magnetic field is generated with a frequency substantially equal to a selected ion precessional magnetic resonance frequency.

* * * * *